United States Patent [19]

Ebel et al.

[11] Patent Number: 5,387,704
[45] Date of Patent: Feb. 7, 1995

[54] PREPARATION OF ANTHRAQUINONES

[75] Inventors: Klaus Ebel, Ludwigshafen; Juergen Schroeder, Viernheim, both of Germany

[73] Assignee: BASF Aktiengesellschaft, Ludwigshafen, Germany

[21] Appl. No.: 150,363

[22] Filed: Nov. 9, 1993

[30] Foreign Application Priority Data

Nov. 11, 1992 [DE] Germany ............... 4238045

[51] Int. Cl.$^6$ ........................................... C07C 221/00
[52] U.S. Cl. .................... 552/238; 552/239; 552/240; 552/241; 552/243; 552/245; 552/246; 552/247; 552/248; 552/251; 552/252; 552/253; 552/254; 552/255; 552/256; 552/260
[58] Field of Search .......................................... 552/238

[56] References Cited

U.S. PATENT DOCUMENTS 3,998,857  12/1976  Oediger .

FOREIGN PATENT DOCUMENTS 2437220  2/1976  Germany .
1351047  4/1974  United Kingdom .
1370413  10/1974  United Kingdom .
2190080  11/1987  United Kingdom .

OTHER PUBLICATIONS

Tetrahedron Letters, vol. 28 (1987) pp. 4529–4532.
Houben–Weyl, Methoden der organischen Chemie, vol. 7/3c, pp. 23–31.

*Primary Examiner*—Johann Richter
*Assistant Examiner*—Rebecca Cook
*Attorney, Agent, or Firm*—John H. Shurtleff

[57] ABSTRACT

Process for preparing amino- and carbamoyl-substituted anthraquinones by Diels-Alder reaction of an N-butadienylcarbamic acid ester of the formula $H_2C=CH-CH=CH-NH-COOR^2$, wherein $R^2$ is alkyl or phenylalkyl, with a 1,4-naphthoquinone or with 1,4-benzoquinone to form a carbamoyl-substituted hydroanthraquinone intermediate and by oxidation of this intermediate with an oxygen-containing gas in a tertiary amine and in the presence of a copper salt to obtain a carbamoyl-substituted anthraquinone product. The Diels-Alder reaction and the oxidation reaction can be carried out as a one-pot synthesis or in separate steps. The carbamic acid ester reactant provides a blocking group represented by $—COOR^2$, and this blocking group is optionally removed by treatment of the carbamoyl-substituted anthraquinone with an alkaline hydroxide solution.

20 Claims, No Drawings

PREPARATION OF ANTHRAQUINONES

The present invention relates to a process for preparing anthraquinones by Diels-Alder reaction of N-butadienylcarbamic acid esters with 1,4-naphthoquinones or with 1,4-benzoquinone, oxidation and, optionally removal of the protective group by treatment with a hydroxide solution.

GB-A-1 370 413 discloses a two-step synthesis of 1-aminoanthraquinone, in which anthraquinone is sulfonated with oleum in the presence of mercury sulfate to give anthraquinone-1-sulfonic acid and this is reacted in a second step with ammonia to give 1-aminoanthraquinone.

GB-A-1 351 047 discloses the nitration of anthraquinone to give 1-nitroanthraquinone and subsequent reduction to 1-aminoanthraquinone.

These processes have the disadvantage that large amounts of salts are produced during the synthesis of 1-aminoanthraquinone.

Tetrahedron Letters Volume 28, (1987) 4529 to 4532 describes the Diels-Alder reaction of 1,4-naphthoquinones with benzyl N-butadienylcarbamates, in which the oxidation to 1-benzyloxycarbonylaminoanthraquinone is carried out using a five-fold excess of activated manganese dioxide and the protective group is removed using hydrobromic acid/acetic acid to give the corresponding 1-aminoanthraquinones.

A disadvantage of this process is the complicated oxidation. The customary processes for the oxidation of tetrahydroanthraquinones from Houben-Weyl, Methoden der organischen Chemie (Methods of Organic Chemistry), Volume 7/3c, pages 23 to 31, such as dehydration in the melt by addition of copper powder, fail with air in the presence of alkali metal hydroxides.

It is an object of the present invention to remedy the abovementioned disadvantages.

We have found that this object is achieved by a novel and improved process for preparing anthraquinones of the general formula I

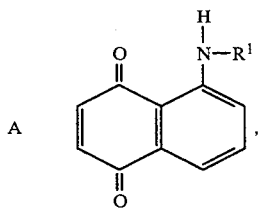

where
$R^1$ is hydrogen or

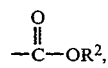

A is

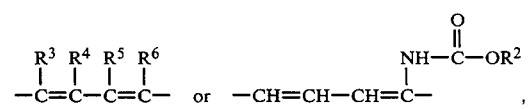

$R^2$ is $C_1$- to $C_8$-alkyl or $C_7$- to $C_{20}$-phenylalkyl and
$R^3$, $R^4$, $R^5$ and $R^6$, independently of one another, are hydrogen, $C_1$- to $C_8$-alkyl, $C_7$- to $C_{20}$-phenylalkyl, $C_1$- to $C_8$-alkoxy, $C_1$- to $C_8$-haloalkyl, nitro, cyano, halogen, amino, $C_1$- to $C_8$-alkylcarbonyl, benzoyl, N-$C_1$- to $C_8$-alkylphenylamino, $C_1$- to $C_8$-alkylsulfonyl, phenylsulfonyl, aminosulfonyl, aminocarbonyl and nitrobenzyl which comprises reacting N-butadienylcarbamic acid esters of the general formula II

where $R^2$ has the abovementioned meanings,
a) in the case in which A is

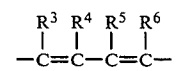

with 1,4-naphthoquinones of the general formula III

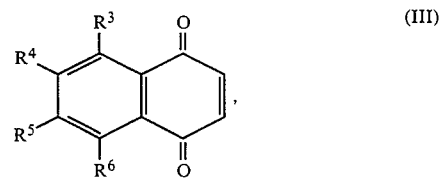

where the substituents $R^3$ to $R^6$ have the abovementioned meanings, or
b) in the case in which A is

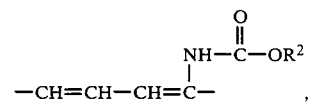

with 1,4-benzoquinone at from 0° to 150° C., and then reacting the resulting carbamoylhydroanthraquinones with oxygen-containing gases in a tertiary amine in the presence of copper salts. Thereafter the resulting carbamoylanthraquinones may be treated with hydroxide solutions at from 0° to 150° C. to remove the protective group $R^1$ when represented by —COOR².

The process according to the invention can be carried out as follows:

Preparation of the 1-carbamoyl-1,4,4a,9a-tetrahydroanthraquinones or the 1,5/1,8-biscarbamoyl-1,4,4a,5,8,8a,9a,10a-octahydroanthraquinones The quinone (1,4-naphthoquinone III or 1,4-benzoquinone) and the N-butadienylcarbamic acid ester II can be introduced in an inert solvent and reacted at from 0° to 150° C., preferably 10° to 100° C., particularly preferably 20° to 70° C. and from 0.01 to 10 bar, preferably 0.1 to 5 bar, particularly preferably at atmospheric pressure.

The molar ratio of the N-butadienylcarbamic acid esters II to the 1,4-naphthoquinones III is 0.5:1–2.5:1 preferably 0.8:1–1.5:1, particularly preferably 0.9:1–1.1:1.

The molar ratio of the N-butadienylcarbamic acid esters II to the 1,4-benzoquinone is 1.5:1–4:1, preferably 1.8:1–3:1, particularly preferably 1.9:1–2.1:1.

Suitable inert solvents are, for example, $C_4$- to $C_{30}$-hydrocarbons such as butanes, pentanes, hexanes, cyclohexane, benzene, toluene, chlorinated hydrocarbons such as dichloromethane, chloroform and trichloroethylene, and pyridine derivatives such as pyridine, picolines (2-, 3- and 4-), lutidines (2,4-, 2,6-, 3,4- and 3,5-), preferably toluene, chloroform and pyridine.

Preparation of the 1-carbamoylanthraquinones or of the 1,5/1,8-bis-carbamoylanthraquinones 1-Carbamoyl-1,4,4a,9a-tetrahydroanthraquinones or 1,5/1,8-bis-carbamoyl-1,4,4a,5,8,8a,9a,10a-octahydroanthraquinones can be oxidized using oxygen-containing gases, for example by introducing gas at from 0° to 150° C., preferably 10° to 100° C., particularly preferably 20° to 50° C., into a tertiary amine, in the presence of copper salts.

Copper salts are employed, as a rule, in a molar ratio from 0.001:1–0.5:1, preferably 0.05:1–0.2:1 to the 1-carbamoyl-1,4,4a,9a-tetrahydroanthraquinone or 1,5/1,8-bis-carbamoyl-1,4,4a,5,8,8a,9a,10a-octahydroanthraquinone.

Suitable oxygen-containing gases are, for example, oxygen gas or preferably the oxygen of the surrounding air.

The two previously described steps can preferably be carried out as a one-pot reaction by reacting the 1,4-naphthoquinones II or 1,4-benzoquinone with N-butadienylcarbamic acid esters III in a tertiary amine in the abovementioned molar ratios at the abovementioned temperatures, in the presence of copper salts in the abovementioned molar ratios, and an oxygen-containing gas.

Useful tertiary amines are, for example, aliphatic amines such as triethylamine, tripropylamine, tetramethylethylenediamine or aromatic amines such as pyridine, picolines (2-, 3- and 4-) and lutidines (2,4-, 2,6-, 3,4- and 3,5-), preferably pyridine.

Useful copper salts are, for example, copper(I) chloride, copper(II) chloride, copper(I) bromide and copper(II) acetate, preferably copper(I) chloride.

Preparation of the 1-aminoanthraquinones of the formula I

The protective group in the 1-carbamoylanthraquinones or in the 1,5/1,8-biscarbamoylanthraquinones can be removed at from 0° to 150° C., preferably from 50° to 100° C., by alkali, for example in aqueous alcoholic hydroxide solution.

Useful alkaline hydroxide solutions are, for example, aqueous alcoholic solutions of alkali metal and/or alkaline earth metal hydroxides such as sodium hydroxide and potassium hydroxide in $C_1$- to $C_8$-alkanols, preferably $C_1$- to $C_4$-alkanols such as methanol, ethanol, n-propanol and isopropanol.

N-Butadienylcarbamic acid esters can be prepared according to Organic Synthesis, Volume 59, (1979) pages 1 to 9.

The connecting link A and the substituents $R^1$, $R^2$, $R^3$, $R^4$, $R^5$ and $R^6$ in the compounds I, II and III independently of one another have the following meanings:

$R^1$ is hydrogen or

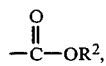

A is

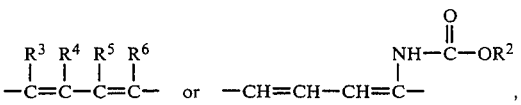

Examples of $R^2$, and $R^3$, $R^4$, $R^5$ and $R^6$ are $C_1$- to $C_8$-alkyl such as methyl, ethyl, n-propyl, isopropyl, n-butyl, isobutyl, sec-butyl, tert-butyl, n-pentyl, isopentyl, tert-amyl, n-hexyl, isohexyl, n-heptyl, isoheptyl, n-octyl and isooctyl, preferably $C_1$- to $C_4$-alkyl such as methyl, ethyl, n-propyl, isopropyl, n-butyl, isobutyl, sec-butyl and tert-butyl, particularly preferably methyl and ethyl, $C_7$- to $C_{20}$-phenylalkyl, preferably $C_7$- to $C_{12}$-phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, 1-phenethyl and 2-phenethyl, $R^3$, $R^4$, $R^5$, $R^6$ may further represent hydrogen $C_1$- to $C_8$-alkoxy such as methoxy, ethoxy, n-propoxy, isopropoxy, n-butoxy, isobutoxy, sec-butoxy, tert-butoxy, n-pentoxy, isopentoxy, tert-amyloxy, n-hexoxy, isohexoxy, n-heptoxy, isoheptoxy, n-octoxy and isooctoxy, preferably $C_1$- to $C_4$-alkoxy such as methoxy, ethoxy, n-propoxy, isopropoxy, n-butoxy, isobutoxy, sec-butoxy and tert-butoxy, particularly preferably methoxy and ethoxy, $C_1$- to $C_8$-haloalkyl, preferably $C_1$- to $C_4$-haloalkyl, particularly preferably $C_1$- to $C_4$-fluoro-, chloro- and/or bromoalkyl such as fluoromethyl, difluoromethyl, trifluoromethyl, chloromethyl, dichloromethyl, trichloromethyl, bromomethyl, dibromomethyl and tribromomethyl, nitro, cyano, halogen such as fluorine, chlorine, bromine and iodine, preferably fluorine, chlorine and bromine, particularly preferably chlorine and bromine, amino, $C_1$- to $C_8$-alkylcarbonyl such as methylcarbonyl, ethylcarbonyl, n-propylcarbonyl, isopropylcarbonyl, n-butylcarbonyl, isobutylcarbonyl, sec-butylcarbonyl, tert-butylcarbonyl, n-pentylcarbonyl, isopentylcarbonyl, tert-amylcarbonyl, n-hexylcarbonyl, isohexylcarbonyl, n-heptylcarbonyl, isoheptylcarbonyl, n-octylcarbonyl and isooctylcarbonyl, preferably $C_1$- to $C_4$-alkylcarbonyl such as methylcarbonyl, ethylcarbonyl, n-propylcarbonyl, isopropylcarbonyl, n-butylcarbonyl, isobutylcarbonyl, sec-butylcarbonyl and tert-butylcarbonyl, particularly preferably methylcarbonyl and ethylcarbonyl, benzoyl, N-$C_1$- to $C_8$-alkylphenylamino such as methylphenylamino, ethylphenylamino, n-propylphenylamino, isopropylphenylamino, n-butylphenylamino, isobutylphenylamino, sec-butylphenylamino, tert-butylphenylamino, n-pentylphenylamino, isopentylphenylamino, tert-amylphenylamino, n-hexylphenylamino, isohexylphenylamino, n-heptylphenylamino, isoheptylphenylamino, n-octylphenylamino and isooctylphenylamino, preferably $C_1$- to $C_4$-alkylphenylamino such as methylphenylamino, ethylphenylamino, n-propylphenylamino, isopropylphenylamino, n-butylphenylamino, isobutylphenylamino, sec-butylphenylamino and tert-butylphenylamino, particularly preferably methylphenylamino and ethylphenylamino, $C_1$- to $C_8$-alkylsulfonyl such as methylsulfonyl, ethylsulfonyl, n-propylsulfonyl, isopropylsulfonyl, n-butylsulfonyl, isobutylsulfonyl, sec-butylsulfonyl, tert-butylsulfonyl, n-pentylsulfonyl, isopentylsulfonyl, tert-amylsulfonyl, n-hexylsulfonyl, isohexylsulfonyl, n-heptylsulfonyl, isoheptylsulfonyl, n-octylsulfonyl and isooctylsulfonyl, preferably $C_1$- to $C_4$-alkylsulfonyl such as methylsulfonyl, ethylsulfonyl, n-propylsulfonyl, isopropylsulfonyl, n-butylsulfonyl, isobutylsulfonyl, sec-butylsulfonyl and tert-butylsulfonyl, particularly preferably methylsulfonyl and ethylsulfonyl, phenylsulfonyl,
aminosulfonyl,
aminocarbonyl and
nitrobenzyl.

1-Aminoanthraquinones are useful intermediates for the preparation of dyestuffs (Ullmanns Encyklopädie der technischen Chemie [Ullmann's Encyclopedia of Industrial Chemistry], 4th edition, Volume 7, pages 586 to 646).

EXAMPLES

Example 1

3.16 g of 1,4-naphthoquinone, 4.48 g of benzyl N-butadienylcarbamate and 50 mg of hydroquinone were dissolved in 100 ml of toluene and stirred at 25° C. for 8 hours and the solution was then concentrated in vacuo. The residue was taken up in chloroform, the solution was filtered through silica gel and the filtrate was concentrated in vacuo. 7.12 g of 1-benzyloxycarbonylamino-1,4,4a,9a-tetrahydroanthraquinone (93% pure; 92% of theory) were obtained.

Example 2

0.47 g of 1-benzyloxycarbonylamino-1,4,4a,9a-tetrahydroanthraquinone, 6 mg of copper(I) chloride and 10 ml of pyridine were stirred at 25° C. for 30 hours under a gentle stream of air and the solution was then concentrated in vacuo. The residue was taken up in chloroform, the solution was extracted with 2N hydrochloric acid and the organic phase was concentrated in vacuo. 0.41 g of 1-benzyloxycarbonylaminoanthraquinone (86% pure; 76% of theory) was obtained.

Example 3

0.50 g of 1-benzyloxycarbonylaminoanthraquinone, 25 ml of ethanol and 25 ml of 50% strength aqueous sodium hydroxide solution were heated under reflux for 6 hours and the solution was then concentrated in vacuo. The residue was taken up in chloroform/water, the phases were separated and the organic phase was washed twice with water. The organic phase was concentrated in vacuo and 0.30 g of 1-aminoanthraquinone (99% pure; 95% of theory) was obtained.

Example 4

0.79 g of 1,4-naphthoquinone, 1.07 g of benzyl N-butadienylcarbamate, 25 mg of copper(I) chloride and 25 ml of pyridine were stirred at 25° C. for 30 hours under a gentle stream of air and the solution was then concentrated in vacuo. The residue was taken up in chloroform, the solution was extracted with 2N hydrochloric acid and the organic phase was concentrated in vacuo. 1.60 g of 1-benzyloxycarbonylaminoanthraquinone (83% pure; 75% of theory) were obtained.

Example 5

0.50 g of 1-benzyloxycarbonylamino-1,4,4a,9a-tetrahydroanthraquinone were dissolved in 100 ml of 5% strength ethanolic potassium hydroxide solution. Air was passed through the solution for 6 hours at 25° C. and the solution was then concentrated in vacuo. The residue was taken up in chloroform/water, the phases were separated and the organic phase was washed twice with water. The organic phase was concentrated in vacuo and unsubstituted anthraquinone was obtained exclusively.

Example 6

0.54 g of p-benzoquinone, 2.03 g of benzyl N-butadienylcarbamate, 99 mg of copper(I) chloride and 50 ml of pyridine were stirred at 25° C. for 44 hours under a gentle stream of air and the solution was then concentrated in vacuo. The residue was taken up in toluene, the solution was extracted with 1N hydrochloric acid and the organic phase was concentrated in vacuo. 2.30 g of 1,8- and 1,5-bis(benzyloxycarbonylamino)anthraquinone (98% pure; 89% of theory) were obtained.

We claim:

1. A process for preparing an anthraquinone of the formula

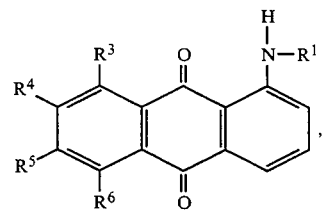

wherein
$R^1$ is hydrogen or

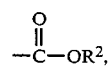

$R^2$ is $C_1$- to $C_8$-alkyl or $C_7$- to $C_{20}$-phenylalkyl, and $R^3$, $R^4$, $R^5$ and $R^6$, independently of one another, are hydrogen, $C_1$- to $C_8$-alkyl, $C_7$- to $C_{20}$-phenylalkyl, $C_1$-to $C_8$-alkoxy, $C_1$- to $C_8$-haloalkyl, nitro, cyano, halogen, amino, $C_1$- to $C_8$-alkylcarbonyl, benzoyl, N-$C_1$- to $C_8$-alkylphenylamino, $C_1$- to $C_8$-alkylsulfonyl, phenylsulfonyl, aminocarbonyl or nitrobenzyl, which process comprises:

reacting an N-butadienylcarbamic acid ester of the formula

where $R_2$ has the abovementioned meanings, with a 1,4-naphthoquinone of the formula

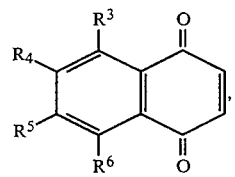

where the substituents $R^3$ to $R^6$ have the abovementioned meanings, at from 0° to 150° and in a molar ratio of the ester II to the 1,4-naphthoquinone III of 0.5:1 to 2.5:1, and reacting the resulting carbamoyltetrahydroanthraquinone with an oxygen-containing gas in a tertiary amine and in the presence of a copper salt.

2. A process as claimed in claim 1, wherein the molar ratio of II:III is 0.8:1 to 1.5:1.

3. A process as claimed in claim 1 wherein the molar ratio of II:III is 0.9:1 to 1.1:1.

4. A process as claimed in claim 1 wherein the reaction of the carbamic acid ester II with the 1,4-naphthoquinone III and the oxidation of the intermediate with an oxygen-containing gas are combined in a one-pot reaction carried out at a temperature of 10° to 100° C., a pressure of 0.01 to 10 bar and a molar ratio of II:III of 0.8:1 to 1.5:1.

5. A process as claimed in claim 4, wherein the molar ratio of I:II is 0.9:1 to 1.1:1.

6. A process as claimed in claim 1, wherein the copper salt is selected from the group consisting of copper (I) chloride, copper (II) chloride, copper (I) bromide and copper (II) acetate.

7. A process as claimed in claim 1, wherein the copper salt is used in a molar ratio, with reference to the carbamoylsubstituted tetrahydroanthraquinone, of from 0.001:1 to 0.5:1.

8. A process as claimed in claim 7 wherein said molar ratio is from 0.05:1 to 0.2:1.

9. A process as claimed in claim 1, wherein the reactants are introduced in an inert solvent.

10. A process as claimed in claim 9, wherein the inert solvent is selected from the group consisting of toluene, chloroform and pyridine.

11. A process for preparing anthraquinones of the formula

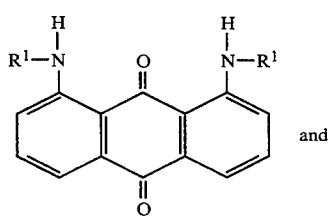

and

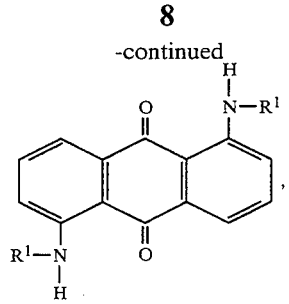

wherein
$R^1$ is hydrogen or

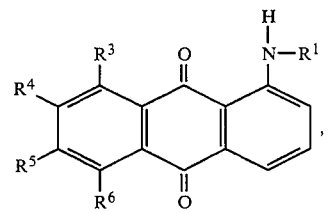

$R^2$ is $C_1$- to $C_8$-alkyl or $C_7$- to $C_{20}$-phenylalkyl and $R^3$, $R^4$, $R^5$ and $R^6$, independently of one another, are hydrogen, $C_1$- to $C_8$-alkyl, $C_7$- to $C_{20}$-phenylalkyl, $C_1$- to $C_8$-alkoxy, $C_1$- to $C_8$-haloalkyl, nitro, cyano, halogen, amino, $C_1$- to $C_8$-alkylcarbonyl, benzoyl, N-$C_1$- to $C_8$-alkylphenylamino, $C_1$- to $C_8$-alkylsulfonyl, phenylsulfonyl, aminocarbonyl or nitrobenzyl, which process comprises:

reacting an N-butadienylcarbamic acid ester of the formula

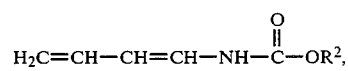

where $R^2$ has the abovementioned meanings, with 1,4-benzoquinone at from 0° to 150° C. and in a molar ratio of the ester II to the 1,4-benzoquinone of 1.5:1 to 4:1 and
reacting the resulting carbamoyloctahydroanthraquinone with an oxygen-containing gas in a tertiary amine and in the presence of a copper salt.

12. A process as claimed in claim 11, wherein the molar ratio of the ester II to 1,4-benzoquinone is 1.8:1 to 3:1.

13. A process as claimed in claim 11, wherein the molar ratio of the ester II to 1,4-benzoquinone is 1.9:1 to 2.1:1.

14. A process as claimed in claim 11, wherein the reaction of the carbamic acid ester II with the 1,4-benzoquinone and the oxidation of the intermediate with an oxygen-containing gas are combined in a one-pot reaction carried out at a temperature of 10° to 100° C., a pressure of 0.01 to 10 bar and a molar ratio of the ester II to 1,4-benzoquinone of 1.5:1 to 4:1.

15. A process as claimed in claim 14 wherein the molar ratio of the ester II to 1,4-benzoquinone is 1.8:1 to 3:1.

16. A process as claimed in claim 11, wherein the copper salt is selected from the group consisting of copper (I) chloride, copper (II) chloride, copper (I) bromide and copper (II) acetate.

17. A process as claimed in claim 11, wherein the copper salt is used in a molar ratio, with reference to the carbamoylsubstituted octahydroanthraquinone, of from 0.001:1 to 0.5:1.

18. A process as claimed in claim 17, wherein said molar ratio is from 0.05:1 to 0.2:1.

19. A process as claimed in claim 11, wherein the reactants are introduced in an inert solvent.

20. A process as claimed in claim 19, wherein the inert solvent is selected from the group consisting of toluene, chloroform and pyridine.

* * * * *

UNITED STATES PATENT AND TRADEMARK OFFICE
CERTIFICATE OF CORRECTION

PATENT NO. : 5,387,704
DATED : February 7, 1995
INVENTOR(S) : Ebel et al.

It is certified that error appears in the above-identified patent and that said Letters Patent is hereby corrected as shown below:

Column 8,
Claim 11, line 12, after "R' is hydrogen or" insert "  "

Column 8,
Claim 11, cancel the entire structural formula which appears in lines 15-22.

Signed and Sealed this

Ninth Day of May, 1995

BRUCE LEHMAN

Attest:

Attesting Officer

Commissioner of Patents and Trademarks